(12) United States Patent
Chang

(10) Patent No.: US 6,924,288 B2
(45) Date of Patent: Aug. 2, 2005

(54) ENANTIOMERICALLY PURE OPIOID DIARYLMETHYLPIPERZINE AND METHODS OF USING SAME

(75) Inventor: Kwen-Jen Chang, Chapel Hill, NC (US)

(73) Assignee: Ardent Pharmaceuticals, Inc., Durham, NC (US)

( * ) Notice: Subject to any disclaimer, the term of this patent is extended or adjusted under 35 U.S.C. 154(b) by 218 days.

(21) Appl. No.: 10/254,609

(22) Filed: Sep. 25, 2002

(65) Prior Publication Data

US 2003/0114462 A1 Jun. 19, 2003

Related U.S. Application Data

(60) Provisional application No. 60/324,712, filed on Sep. 25, 2001.

(51) Int. Cl.[7] .................. C07D 409/06; A61K 31/496; A61P 1/12; A61P 11/14; A61P 25/04
(52) U.S. Cl. .................. 514/252.13; 544/379
(58) Field of Search ...................... 514/252.13; 544/379

(56) References Cited

U.S. PATENT DOCUMENTS

| | | | |
|---|---|---|---|
| 5,658,908 A | 8/1997 | Chang et al. ............... | 514/252 |
| 5,807,858 A | 9/1998 | Chang et al. ............... | 514/255 |
| 5,854,249 A | 12/1998 | Chang et al. ............... | 514/255 |
| 2002/0052007 A1 | 5/2002 | Chang et al. | |

FOREIGN PATENT DOCUMENTS

WO    WO 93/15062    8/1993

OTHER PUBLICATIONS

Knapp, Richard J.; Santoro, Giovanna; De Leon, Irene A.; Lee, Katharine B.; Edsall, Sidney A.; Waite, Sue; Malatynska, Ewa; Varga, Eva; Calderon, Silvia N.; et al. Journal of Pharmacology and Experimental Therapeutics, 277(3), 1284–1291 (English) 1996.*

Calderon, Silvia N.; Rothman, Richard B.; Porreca, Frank; Flippen–Anderson, Judith L.; McNutt, Robert W.; Xu, Heng; Smith, Larren E.; Bilsky, Edward J.; Davis, Peg; Rice, Kenner C.; Journal of Medicinal Chemistry, 37(14), 2125–8 (English) 1994.*

Corbett, A. et al, "Opioid Receptors", [online] no date, [retrieved on May 27, 2004]. Retrieved from the internet, <http://opioids.com/receptors/>.*

Mike Hamilton, "FAQ–Opioid", [online] 1994, [retrieved on May 27, 2004]. Retrieved from the internet, <http://opioids.com/opioidfaq/faq.html>.*

Boswell, et al. Synthesis, stereochemistry, and opioid receptor binding activity of heterocyclic analogues of BW373U86. J. Heterocyclic Chem., 32, 1801 (1995).

* cited by examiner

*Primary Examiner*—Thomas C. McKenzie
(74) *Attorney, Agent, or Firm*—Marianne Fuierer; Steven J. Hultquist

(57) ABSTRACT

An essentially pure compound of the formula:

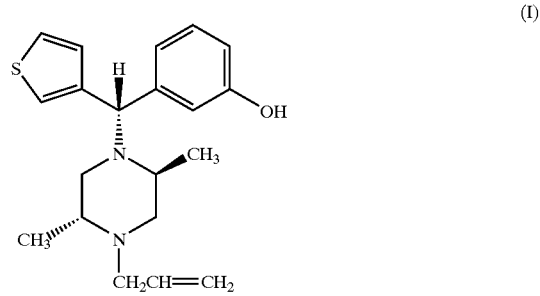

(I)

(–)3-((S)-((2S,5R)-4-allyl-2,5-dimethyl-1-piperazinyl)(3-thienyl)methyl)phenol or a pharmaceutically acceptable salt thereof, having utility as a receptor-binding species, e.g., as a therapeutic agent for mediating analgesia; as a co-administered agent with various other bioactive compositions, including anesthetics, barbiturates, analgesics, etc.; for reducing, treating, reversing or preventing drug-mediated respiratory depression that may be directly or indirectly caused by use of such various bioactive compositions; as a conjugate in agonist/antagonist pairs for verifying/assaying receptor and neurotransmitter function; and as a therapeutic agent having utility in combating pain, cardiac disorders, mental and emotional disorders cough, diarrhea and gastro-intestinal disorders.

18 Claims, 6 Drawing Sheets

ENANTIOMERICALLY PURE OPIOID DIARYLMETHYLPIPERZINE AND METHODS OF USING SAME

CROSS-REFERENCE TO RELATED APPLICATIONS

This application claims priority from U.S. Provisional Patent Application No. 60/324,712 filed on Sep. 25, 2001 in the name of Kwen-Jen Chang for "AN ENANTIOMERICALLY PURE OPIOID DIARYLMETHYLPIPERZINE AND METHODS OF USING SAME."

BACKGROUND OF THE INVENTION

1. Field of the Invention

The present invention relates to a novel, essentially enantiomerically pure diarylmethylpiperazine compound having utility as a receptor-binding species, e.g., as a mu and/or delta receptor opioid compound mediating analgesia; as a therapeutic agent for co-administration with various other bioactive compositions, including anesthetics, barbiturates, analgesics, etc. for reducing, treating, reversing or preventing drug-mediated respiratory depression that may be directly or indirectly caused by use of such various bioactive compositions; as a conjugate in agonist/antagonist pairing for verifying/assaying receptor and neurotransmitter function; and as a therapeutic agent having utility in combating drug addiction, alcohol addiction, cardiac disorders, drug overdose, mental illness, cough, lung edema, diarrhea, respiratory, and gastro-intestinal disorders.

2. Description of Related Art

In the study of opioid biochemistry, a variety of endogenous opioid compounds and non-endogenous opioid compounds has been identified. In this effort, significant research has been focused on understanding the mechanism of opioid drug action, particularly as it relates to cellular and differentiated tissue opiate receptors.

Opioid drugs typically are classified by their binding selectivity in respect of the cellular and differentiated tissue receptors to which a specific drug species binds as a ligand. These receptors include mu ($\mu$), delta ($\delta$), sigma ($\sigma$) and kappa ($\kappa$) receptors.

The well-known narcotic opiates, such as morphine and its analogs, are selective for the opiate mu receptor. Mu receptors mediate analgesia, respiratory depression, and inhibition of gastrointestinal transit; kappa receptors mediate analgesia and sedation: and sigma receptors mediate various biological activities.

The existence of the opioid delta receptor is a relatively recent discovery which followed the isolation and characterization of endogenous enkephalin peptides which are ligands for the delta receptor. Research in the past decade has produced significant information about the delta receptor. Delta receptors mediate analgesia, but do not appear to inhibit intestinal transit in the manner characteristic of mu receptors.

Opioid agents frequently are characterized as either agonists or antagonists. Agonists and antagonists are agents which recognize and bind to receptors, affecting (either initiating or blocking) biochemical/physiological sequences, a process known as transduction. Agonists inhibit or suppress neurotransmitter outputs in tissues containing receptors, e.g., inhibiting pain responses, or affecting other output-related phenomena. Antagonists also bind to receptors, but do not inhibit neurotransmitter outputs. Thus, antagonists bind to the receptor sites and block the binding of agonist species which are selective for the same receptor.

Opioid diarylmethylpiperazines having both mu and delta receptor activity have been described in U.S. Pat. No. 5,658,908 (Chang et al.). However, the synthesis of these compounds in the laboratory, having at least one asymmetric carbon atom, invariably leads to a racemic mixture exhibiting no optical activity. In contrast, naturally occurring compounds which possess an asymmetric carbon atom almost invariably are optically active.

In describing an optically active compound, the prefixes D and L or R and S are used to denote the absolute configuration of the molecule about its chiral center(s). The prefixes (+) and (−) or d and l are employed to designate the direction of rotation of plane-polarized light by the compound, with (−) or l meaning that the compound is levorotatory. A compound prefixed with (+) or d is dextrorotatory. Many organic compounds exist in optically active forms, i.e., they have the ability to rotate the plane of plane-polarized light.

For a given chemical structure, different optically active compounds are called stereoisomers and are identical except that they are mirror images of one another. A specific stereoisomer may also be referred to as an enantiomer, and a mixture of such isomers is called an enantiomeric or racemic mixture.

Stereochemical purity is of importance in the field of pharmaceuticals, where many of the most prescribed drugs exhibit chirality. An illustrative example is the l-form of propranolol, which is known to be 100 times more potent than the d-enantiomer. Furthermore, optical purity is important since certain isomers may actually be deleterious rather than simply inert. For example, it has been suggested that the d-enantiomer of thalidomide is a safe and effective sedative when prescribed for the control of morning sickness during pregnancy and that the corresponding l-enantiomer is a potent teratogen.

Whereas the foregoing Chang et al. patent recognized that diarylmethylpiperazines may have optically active forms and individual enantiomeric forms may be synthesized, no example of the presently claimed optically active form was given. Although it was generally concluded heretofore that the described diarylmethylpiperazines racemic mixtures and inclusive enantiomers exhibited similar activity, it has been discovered by the present inventors that there are substantial unforeseen advantages in the use of an enantiomerically pure diarylmethylpiperazine of the present invention.

SUMMARY OF INVENTION

The present invention relates to a compound having the structure of formula (I):

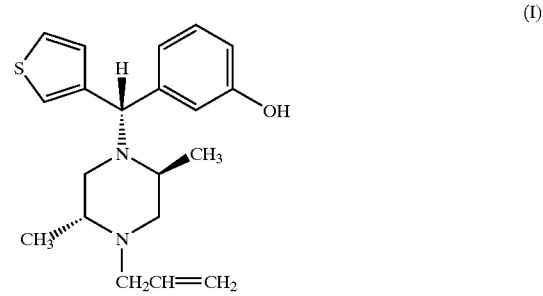

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof.

Examples of pharmaceutically acceptable esters of the compound of formula (I) include carboxylic acid esters of the hydroxyl group in the compound of formula (I) in which the non-carbonyl moiety of the carboxylic acid portion of the ester grouping is selected from straight or branched chain alkyl (e.g., n-propyl, t-butyl, n-butyl), alkoxyalkyl (e.g., methoxymethyl), arylalkyl (e.g., benzyl), aryloxyalky (e.g., phenoxymethyl), and aryl (e.g., phenyl); alkyl-, aryl-, or arylalkylsulfonyl (e.g., methanesulfonyl); amino acid esters (e.g., L-valyl or L-isoleucyl); dicarboxylic acid esters (e.g., hemisuccinate); carbonate esters (e.g., ethoxycarbonyl); carbamate esters (e.g., dimethylaminocarbonyl, (2-aminoethyl)aminocarbonyl); and inorganic esters (e.g., mono-, di- or triphosphate).

Examples of pharmaceutically acceptable salts of the compound of formula (I) include salts derived from an appropriate base, such as an alkali metal (for example, sodium, potassium), an alkaline earth metal (for example, calcium, magnesium), ammonium and $NX_4^+$ (wherein X is $C_1$–$C_4$ alkyl). Pharmaceutically acceptable salts of an amino group include salts of: organic carboxylic acids such as acetic, citric, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4^+$, or $NX_4^+$ (wherein X is for example a $C_{1-4}$ alkyl group).

For therapeutic use, salts of the compound of formula (I) will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

The compound of formula (I) has utility as an exogenous receptor combinent compound, and can be used for binding with an opioid receptor. Further, the compound can be a conjugate in an agonist/antagonist pair which may be employed for transductional assay of neurotransmitter function in appertaining cellular or differentiated tissue systems. In addition to receptor assay, differential binding, and specificity applications for cellular, histological, and corporeal monitoring and assessment purposes, the compound of the above formula (I) exhibits specific bioactivity characteristics rendering it useful as a treatment agent for various physiological and pathological conditions.

The molecule of formula (I) mediates analgesia with reduced respiratory depression, and further is useful for the treatment of diarrhea, mental illness, apnea, cognitive disorders, cardiac disorders, cough, lung edema, gastrointestinal disorders, spinal injury, and drug addiction.

Further, the present invention relates in one aspect to a pharmaceutical composition comprising (i) a mu receptor agonist therapeutic agent mediating a respiratory, muscular or nausea side effect and (ii) an effective amount for reducing, treating or preventing the side effects, of a compound of the formula:

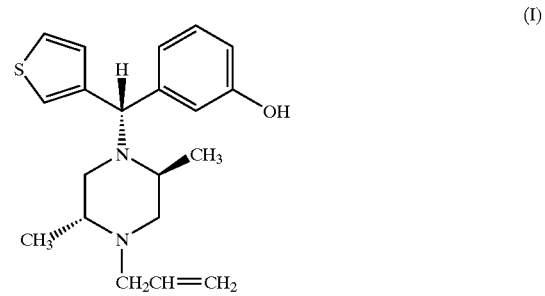

(I)

(−)-3-((S)-((2S,5R)-4-allyl-2,5-dimethyl-1-piperazinyl)(3-thienyl)methyl)phenol, or esters or salts thereof.

In addition, to the extent that degeneration or dysfunction of opioid receptors is present or implicated in a disease state involving tissue or discrete cellular loci, isotopically labeled versions of the opioid compound of the present invention may find utility in diagnostic and imaging applications, e.g., diagnostic techniques involving positron emission tomography (PET) scans of the brain.

Another aspect of the present invention encompasses a method of mediating analgesia comprising administering an effective amount of an opioid receptor agonist compound of the formula:

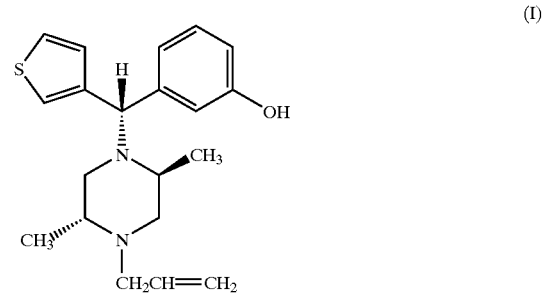

(I)

(−)-3-((S)-((2S,5R)-4-allyl-2,5-dimethyl-1-piperazinyl)(3-thienyl)methyl)phenol, or esters or salts thereof.

The compound of formula (I) may be administered in a pharmaceutically acceptable carrier.

Yet another aspect of the present invention relates to method of treating a patient in need thereof with an opioid mu receptor agonist therapeutic agent, while attenuating respiratory depression incident to the administration thereof, comprising administering to the patient with said opioid mu receptor agonist therapeutic agent, an effective amount of an opioid receptor agonist to attenuate the respiratory depression, the opioid receptor agonist compound having the formula:

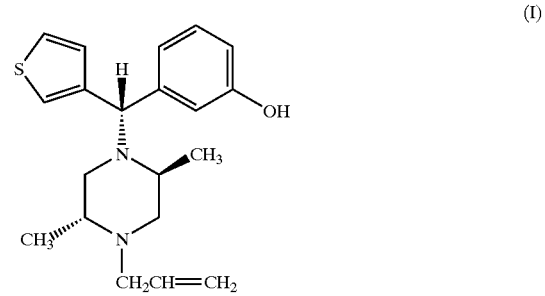

(I)

(−)-3-((S)-((2S,5R)-4-allyl-2,5-dimethyl-1-piperazinyl)(3-thienyl)methyl)phenol, or esters or salts thereof.

Yet another aspect of the present invention relates to a pharmaceutical composition comprising:

(a) an effective amount of a bioactive agent for treatment of a condition selected from the group consisting of drug addiction, alcohol addiction, drug overdose, mental illness, cough, lung edema, gastro-intestinal disorders, arthritis, psoriasis, asthma, inflammatory bowel disease, disorders of respiratory function, functional bowel disease, irritable bowel syndrome, diarrhea, functional distension, functional pain, non-ulcerogenic dyspepsia, organ transplant rejection, skin graft rejection, cardiac disorders, mental disorders, emotional disorders, cognitive disorders; emesis; respiratory depression; acne and skin lesions; and (b) an effective amount of a compound comprising the formula:

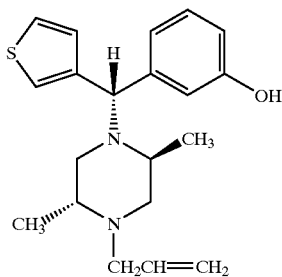

(I)

(-)3-((S)-((2S,5R)-4-allyl-2,5-dimethyl-1-piperazinyl)(3-thienyl)methyl)phenol or a pharmaceutically acceptable salt or esters thereof.

DETAILED DESCRIPTION OF THE INVENTION

Figure 1:
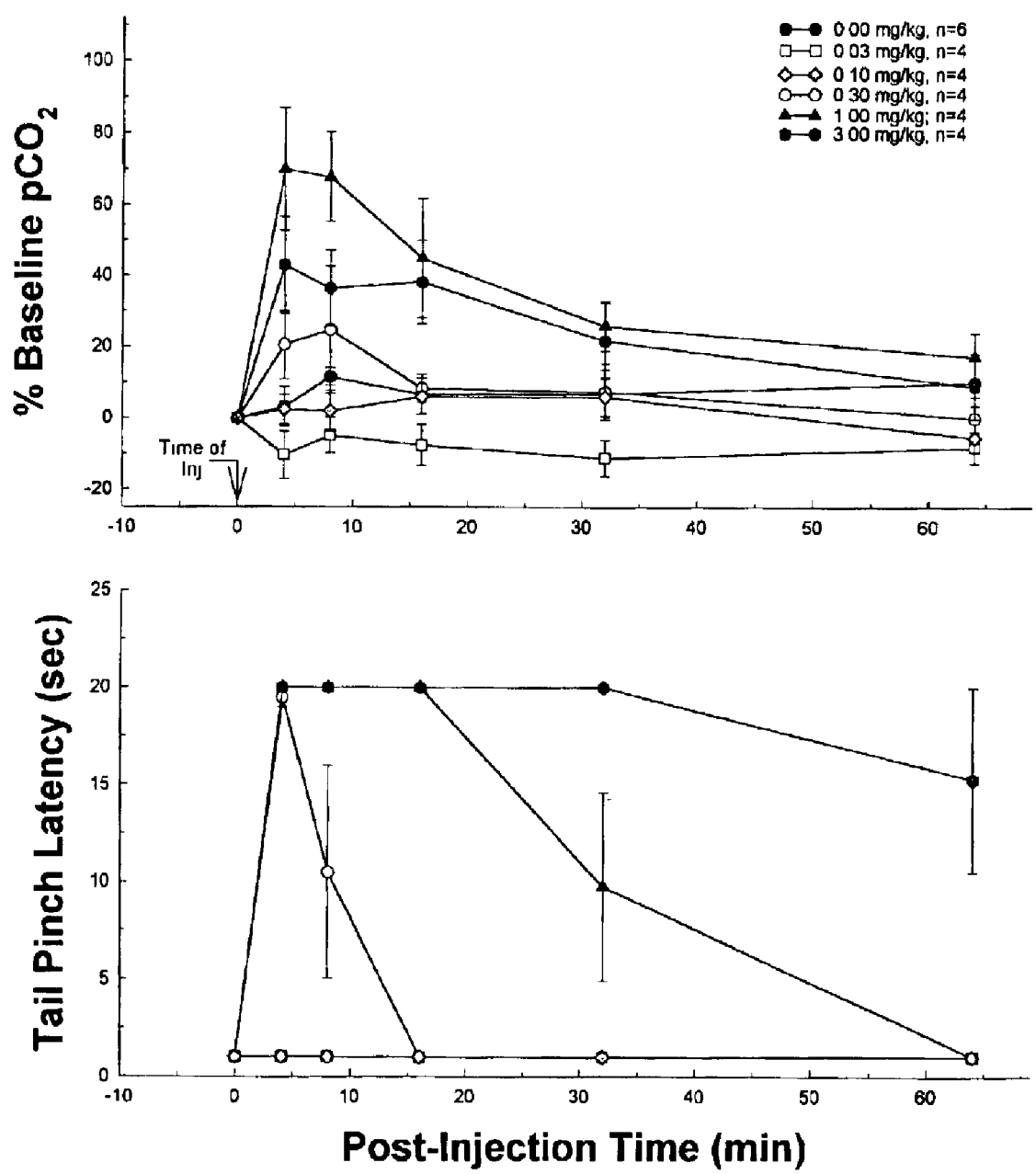
FIG. 1 shows the effects of racemic mixture DPI-1197W92 on analgesia and respiratory depression in test animals.

The present invention relates to an essentially enantiomerically pure compound of the formula:

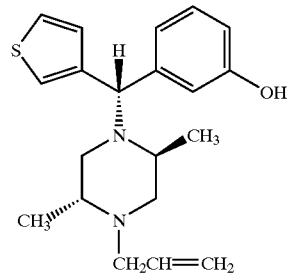

(I)

(-)3-((S)-((2S,5R)-4-allyl-2,5-dimethyl-1-piperazinyl)(3-thienyl)methyl)phenol, or esters or salts thereof.

The compound of formula (I), sometimes hereinafter referred to as DPI-125, acts as a delta-opioid agonist in the mouse vas deferens delta receptor subtype, as well as an agonist at the delta receptor in the mouse brain, an empirically distinguishable delta receptor subtype from the delta receptor in the mouse vas deferens. The compound has activity at the mu-opioid receptor and exhibits some affinity for the kappa receptor.

In in vitro tests for agonist/antagonist activity, such as receptor binding affinity tests, and inhibition of electrically stimulated muscle twitch tests, the compound of formula (I) exhibits potency over a range of from nanomolar to micromolar concentrations.

The compound of formula (I) and esters and salts thereof have pharmaceutical activity, including, inter alia, analgesic activity, and is useful in treating animals, e.g., mammals such as humans, for conditions in which analgesia is desired.

A method of treating pain in an animal in need of such treatment comprises administering to the animal an effective analgesia-inducing amount of a compound of formula (I) or an ester or salt thereof.

In addition, the compound of formula (I) and esters or salts thereof have appertaining therapeutic utility for treatment of conditions including: preventing or treating inflammatory diseases such as arthritis, psoriasis, asthma, or inflammatory bowel disease, disorders of respiratory function, gastrointestinal disorders such as functional bowel disease, functional GI disorders such as irritable bowel syndrome, functional diarrhea, functional distension, functional pain, non-ulcerogenic dyspepsia or others associated with disorders of motility or secretion, as analgesics for treating pain including non-somatic pain, as immunosuppressants to prevent rejection in organ transplant and skin graft, cardiac disorders, drug and alcohol addiction/overdose, mental, emotional, and cognitive disorders; cough; lung edema; emesis, respiratory depression; and gastrointestinal disorders.

Correspondingly, the present invention contemplates a method of treating an animal subject having such condition(s) and in need of such treatment, comprising administering to such animal an effective amount of a compound of the present invention which is therapeutically effective for said condition.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered the compound of formula (I) at any suitable therapeutically effective and safe dosage, as may readily be determined within the skill of the art, and without undue experimentation.

In general, while the effective dosage of the compound of the invention for therapeutic use may be widely varied in the broad practice of the invention, depending on the specific application, condition, or disease state involved, as readily determinable within the skill of the art, suitable therapeutic doses of the formula (I) compound or esters or salts thereof, for each of the appertaining compositions described herein, and for achievement of therapeutic benefit in treatment of each of the conditions described herein, typically will be in the range of 1 microgram ($\mu$g) to 100 milligrams (mg) per kilogram body weight of the recipient per day, preferably in the range of 5 $\mu$g to 75 mg per kilogram body weight per day, and most preferably in the range of 10 $\mu$g to 50 mg per kilogram body weight per day.

The desired dose is preferably presented as two, three, four, five, six, or more sub-doses administered at appropriate intervals throughout the day. These sub-doses may be administered in unit dosage forms, for example, containing from 10 $\mu$g to 1000 mg, preferably from 50 $\mu$g to 500 mg, more preferably from 50 $\mu$g to 250 mg, and most preferably from 50 $\mu$g to 10 mg of active ingredient per unit dosage form. Alternatively, if the condition of the recipient so requires, the doses may be administered as a continuous infusion.

The mode of administration and dosage forms will of course affect the therapeutic amount of the compound that is desirable and efficacious for the given treatment application.

For example, orally administered dosages typically are at least twice, e.g., 2–10times, the dosage levels used in parenteral administration methods, for the same active ingredient. In oral administration for inducing analgesia, dosage levels for the compound(s) of the invention may be on the order of 5–200 mg/70 kg body weight/day. Intrathecal administration dosage levels generally are on the order of about 10% of the levels characteristic of parenteral administration dosage levels. In tablet dosage forms, typical active agent dose levels suitable for inducing analgesia are on the order of 10–100 mg per tablet.

The compound of formula (I) may be administered per se as well as in the form of pharmaceutically acceptable ethers, esters, salts, and other physiologically functional derivatives thereof.

The present invention also contemplates pharmaceutical formulations, both for veterinary and for human medical use, which comprise as the active agent the molecule of formula (I).

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, nasal, ophthalmic, subcutaneous, intramuscular, intravenous, transdermal, spinal, intrathecal, intra-articular, intra-arterial, sub-arachnoid, sublingual, oral mucosal, bronchial, lymphatic, and intra-uterine administration. Formulations suitable for parenteral and oral administration are preferred.

When the active agent of formula (I) is utilized in a formulation comprising a liquid solution, the formulation advantageously may be administered parenterally. When the active agent is employed in a liquid suspension formulation, the formulation may be advantageously administered orally, rectally, or bronchially.

When the active agent is utilized directly in the form of a powdered solid, the active agent may advantageously be administered orally or sublingually. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active compound of formula (I) in a "vectorized" form, such as by encapsulation of the active agent in a liposome or other encapsulant medium, or by fixation of the active compound, e.g., by covalent bonding, chelation, or associative coordination, on a suitable biomolecule, such as those selected from proteins, lipoproteins, glycoproteins, and polysaccharides.

The formulations comprising the active compound of formula (I) may conveniently be presented in unit dosage forms and may be prepared by any of the methods well known in the art of pharmacy. Such methods generally include the step of bringing the active compound into association with a carrier which constitutes one or more accessory ingredients. Typically, the formulations are prepared by uniformly and intimately bringing the active compound into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration comprise a sterile aqueous preparation of the active compound, which preferably is isotonic with the blood of the recipient (e.g., physiological saline solution). Such formulations may include suspending agents and thickening agents, liposomes or other microparticulate systems which are designed to target the compound to blood components or one or more organs. The formulations may be presented in unit-dose or multi-dose form.

Nasal spray formulations comprise purified aqueous solutions of the active compound of formula (I) with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound of formula (I) dissolved or suspended in one or more media, such as mineral oil, petroleum, polyhydroxy alcohols, or other bases used for topical pharmaceutical formulations.

Transdermal formulations may be prepared by incorporating the active agent of formula (I) in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The present invention also contemplates a process for the preparation of (−)3-((S)-((2S,5R)-4-allyl-2,5-dimethyl-1-piperazinyl)(3-thienyl)methyl)phenol or an ester or salt thereof to synthesize an essentially enantiomerically pure opioid receptor agonist that is substantially free of its stereoisomer.

Such compound is desirably prepared in substantially pure enantiomer form, with an enantiopurity of at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

The enantiomerically pure compound of the present invention can be co-administered with a bioactive agent that mediates respiratory depression such as a mu receptor agonist, i.e., various analgesics, and aesthetics, and barbiturates. The vast majority of currently used high potency analgesics, including morphine, alfantanil, morphine-6-glucoronide, oxymorphone, hydromorphone, oxycodone, hydrocodone, fentanyl, meperidine, sufentanyl and codeine, are mu receptor binding compounds. As is well established, these compounds, while highly efficacious for mediating analgesia, have accompanying side effects, including respiratory depression. The use of (−)3-((S)-((2S,5R)-4-allyl-2,5-dimethyl-1-piperazinyl)(3-thienyl)methyl)phenol or ester or salt thereof according to the present invention may prevent, reduce, attenuate or even eliminate or reverse conditions in which analgesia induces respiratory depression, such as the respiratory depression side effects normally attendant to the use of mu receptor binding compounds.

Thus, the present invention contemplates co-administration of (−)3-((S)-((2S,5R)-4-allyl-2,5-dimethyl-1-piperazinyl)(3-thienyl)methyl)phenol with drug agents mediating respiratory depression, in which the compound of the present invention is administered in an amount effective to combat, e.g., significantly attenuate, and preferably substantially eliminate, the respiratory depression incident to the use of the respiratory depression-mediating agent.

Thus, the compounds of the invention have broad utility in surgical and clinical care applications, to combat the unwanted respiratory depression side effect incident to the use of such commonly used drugs as morphine and fentanyl.

Further, the present invention provides pharmaceutical compositions comprising a combination of an effective amount of an opiate analgesic and an effective amount of (−)3-((S)-((2S,5R)-4-allyl-2,5-dimethyl-1-piperazinyl)(3-thienyl)methyl)phenol or an ester or salt thereof, in a composition for combating the respiratory depression effect of a respiratory depression-mediating agent. The use of the claimed compound for combating respiratory depression, and in combination "cocktail" pharmaceutical compositions, is more fully discussed below.

In such a combination of the opiate agent (or other respiratory depression-mediating compound), and a respiratory depression-combating compound of formula (I) or an ester or salt thereof, the dosage of the opiate agent for inducing analgesia, and the dosage of the formula (I) compound or ester or salt thereof for reducing, treating or preventing respiratory depression, can be independently determined. The separate control of dosages for these two functions provides for greater flexibility in treating individual patients. This separate control is one of the advantages of combination pharmaceutical compositions of the present invention.

The combination pharmaceutical compositions of the present invention thus comprise a combination of (1) an effective amount of a therapeutic agent having a respiratory depression (side) effect, e.g., an opiate analgesic, and (2) an effective amount of (−)3-((S)-((2S,5R)-4-allyl-2,5-dimethyl-1-piperazinyl)(3-thienyl)methyl)phenol or ester or salt thereof, for reducing, treating or preventing respiratory depression.

In addition to methods mediating analgesia and treating, reducing or preventing respiratory depression, the present invention also provides methods for screening and characterizing respiratory depression-suppressing compounds, comprising conducting activity reversal assays of candidate respiratory depression-suppressing compounds which in receptor tissue transductionally mediate a respiratory depression suppressing effect in response to a respiration-depressing composition.

The activity reversal assays are conducted comparatively, in the absence and in the presence of an anti-suppression compound of formula (I) or an ester or salt thereof, to determine if the (respiratory depression) suppressing activity of the candidate compound is markedly reversed in the receptor system by the presence of the anti-suppression compound of formula (I) or an ester or salt thereof. If so, the assay indicates the candidate respiratory depression-suppressing compound as possessing potential bioefficacy for suppressing respiratory depression effects incident to the use of other therapeutic agents.

The present invention is further defined by reference to the following examples describing in detail the preparation of the compound and compositions comprising same. It will be apparent to those skilled in the art that many modifications may be practiced without departing from the purpose and intent of the invention.

EXAMPLE 1

Set out below is the synthesis scheme for production of (−)3-((S)-((2S,5R)-4-allyl-2,5-dimethyl-1-piperazinyl)(3-thienyl)methyl)phenol.

A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230–400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, CDCl$_3$): δ 0.2 (s,6H); 1.0 (s,9H); 6.75 (m,1H); 7.0 (br s, 1H); 7.1 (m,2H).

3-tert-Butyldimethylsilyloxyphenylmagnesium bromide was formed by the slow addition of a mixture 3-bromophenoxy-tert-butyldimethylsilane (118 g, 400 mmol) and dibromoethane (15 g, 80 mmol) in 400 mL of inhibitor-free anhydrous tetrahydrofuran to a solution of magnesium turnings (15.5 g, 640 mmol) in 800 mL of inhibitor-free anhydrous tetrahydrofuran at reflux. After stirring for one hour at reflux the light brown clear mixture was cooled to room temperature.

Doubly distilled thiophene-3-carboxaldehyde (2.46 g, 22 mmol), benzotriazole (2.62 g, 22 mmol), (2R,5S)-1-allyl-2,5-trans-dimethylpiperazine (3.39 g, 22 mmol, Chirotech Technology, Ltd., Cambridge, England) and p-toluenesulfonic acid monohydrate (209 mg, 1.1 mmol) were dissolved in 125 mL toluene and heated to a gentle reflux. The water-toluene azeotrope was collected in a Dean-Stark trap over the course of 2.5 hours. The remaining solvent was removed under vacuum. The residue was dissolved in 25 mL anhydrous inhibitor-free tetrahydrofuran and to this was added a solution of 3-tert-butyldimethylsilyloxyphenylmagnesium bromide in tetrahydrofuran (125 mL, 0.32 M) under a nitrogen atmosphere at 20–25° C.

The reaction was stirred at 40° C. for 2 hours and then quenched by the addition of 25 mL of saturated NH$_4$Cl solution. Anhydrous magnesium sulfate (~5 g) and Celite (~10 g) were added. The mixture was stirred and filtered, and the solvent was removed under reduced pressure. The residue was dissolved in ethyl acetate (200 mL) and washed with 1 N NaOH solution (3×100 mL), water (1×100 mL) and brine (1×100 mL). The solution was then concentrated under reduced pressure.

The dark residue was dissolved in 50 mL anhydrous tetrahydrofuran and tetrabutyl-ammonium fluoride dihydrate (8.63 g, 33 mmol) was added. After stirring for 2 hours the reaction was concentrated and the residue was dissolved in 100 mL of ethyl acetate. The mixture was extracted with dilute NaHCO$_3$ solution (3×75 mL) and with water (1×75 mL). The organic layer was diluted with 100 mL of methyl t-butyl ether and extracted with 1% citric acid solution (3×100 mL). The combined aqueous extracts were vacuum filtered through a 0.45 micron membrane filter and the filtrate adjusted to pH 8.5 using 50% NaOH solution before it was extracted with dichloromethane (2×100 mL). The solution was dried azeotropically when concentrated under reduced pressure. The resulting tan glassy solid (3.6 g, 10.5 mmol, 47.8%) was crystallized from 43 mL of 45:55/2-propanol: water and recrystallized from 20 mL of 1:1/2-propanol: water to yield fluffy, white needle crystals (2.1 g, 6.13 mmol, 28% based on chiral piperazine), $[\alpha]_D^{20}$=−8.33° (abs. ethanol, c=1.0).

$^1$H NMR (500 MHz, d$_6$-DMSO): δ 9.32 (s, 1 H), 7.44 (dd, J=3.2, 4.9 Hz, 1 H), 7.15 (s,1 H), 7.13 (t, J=8.25 Hz, 1 H), 6.98 (d, J=4.9 Hz, 1 H), 6.66–6.70 (m, 3 H), 5.73–5.81 (m, 1 H), 5.15 (d, J=17.1 Hz, 1 H), 5.09 (d, J=10.5 Hz, 1 H), 5.02 (s, 1 H), 3.20 (br d, J=10.2 Hz, 1 H), 2.78 (dd, J=7.3, 7.5 Hz, 1 H), 2.68 (dd, J=2.6, 11.3 Hz, 1 H), 2.59 (dd, J=1, 9.3 Hz, 1 H), 2.44 (br s, 2 H), 2.02 (t, J=8.6 Hz, 1 H), 1.81 (t, J=8.1 Hz, 1 H), 1.09 (d, J=6 Hz, 3 H), 0.91 (d, J=6 Hz, 3 H).

Calculated for C$_{20}$H$_{26}$N$_2$OS: C, 70.14; H, 7.65; N, 8.18; S, 9.36%. Found: C,70.19; H, 7.58; N, 8.12; S, 9.33%.

The present invention encompasses the above synthesized compound and use thereof wherein the compound of formula (I) has unexpected potency when compared to the racemic mixture including same or its enantiomer. It may be assumed at first impression that all enantiomers and/or the racemic mixtures would have similar in vivo or in vitro profiles, however, this is not invariably the case, as shown in the following Examples 2–6.

EXAMPLE 2

Two stereoisomerically related racemic mixtures and inclusive enantiomers were evaluated for in vitro opioid receptor affinity in rat brain membranes (μ and δ opioid) and guinea pig cerebellum (κ opioid receptor). Membranes for radioligand binding were prepared from either rat whole brain or guinea pig cerebellum, supplied by Pel-Freeze Biological Inc. (Rogers, Ark.). Tissues were homogenized in 50 mM TRIS (Tris[hydrooxymethyl]aminomethane) buffer (pH 7.4) containing 50 ug/ml soybean trypsin inhibitor, 1 mM EDTA (Ethylenediaminetetraacetic acid), and 100 μM PMSF (Phenylmethylsulfonyl fluoride). The homogenized brain tissues were centrifuged at 500×g for 30 minutes (4° C.) to remove large debris. The supernatant was polytronically sonicated for 10 seconds (P.E. setting of 2, 4° C.). Sucrose solution was then added to a final concentration of 0.35 M using a 10 mM TRIS-Sucrose buffer (pH 7.4) and the brain membranes were then centrifuged at 40,000×g for 30 minutes (4° C.). The membrane pellets were then washed twice in 10 mM TRIS buffer (pH 7.4) containing 50 μg/ml soybean trypsin inhibitor, 1 mM EDTA, and 100 μM PMSF.

Radioligand binding assays were performed in 10 mM TRIS buffer (pH 7.4) containing 50 μg/ml soybean trypsin inhibitor, 1 mM EDTA, 5 mM MgCl$_2$, and 100 μM PMSF. Tritium-labeled DAMGO (μ), Deltorphin II (δ), or U69593 (κ) purchased from New England Nuclear were used as ligands in competitive experiments (2–3×10$^{-10}$ M final concentrations) with non-specific binding defined by 0.5× 10$^{-6}$ M Naloxone (purchased from SIGMA Chemical Co.). All binding assays were run at room temperature for 90 minutes and then terminated by rapid filtration on GF/C glass fiber filters (Whatman, Hillsboro, Oreg.) with 50 mM TRIS buffer (4° C., pH 7.4) employing a Brandel Semi-automatic Cell Harvester (Model M48, Brandel, Gaithersburg, Md.). The filters were washed twice with 50 mM TRIS buffer (4° C., pH 7.4) and the filters were placed in liquid scintillation cocktail and the bound radioactivity counted on a Beckman LS 6500 scintillation counter. The potency of the compounds in inhibiting the binding of radiolabelled DAMGO (μ), Deltorphin II (δ), or U69593 (κ) was determined from full concentration-effect curves. With the computer program Prism (GraphPad Software Inc., San Diego, Calif.) the IC$_{50}$ values were determined using a one-site nonlinear regression analysis of the radioligand binding data. The $IC_{50}$ values were then converted to $K_i$ values using the Cheng-Prusoff equation. (Cheng Y and Prusoff W H (1973) Relationship between the inhibition constant (K1) and the concentration of inhibitor which causes 50 percent inhibition (I50) of a enzymatic reaction. Biochem Pharm 22:3099–3108.)

The following compounds were tested:

Compound 1
(DPI-1197W92) A racemic mixture (±)3-((R*)-((2R*, 5S*)-4-allyl-2,5-dimethyl-1-piperazinyl)(3-thienyl)methyl) phenol which includes enantiomers (−)3-((S)-((2S,5R)-4-allyl-2,5-dimethyl-1-piperazinyl)(3-thienyl)methyl)phenol and (+)3-((R)-((2R,5S)-4-allyl-2,5-dimethyl-1-piperazinyl) (3-thienyl)methyl)phenol (RRS and SSR).

Compound 2
(DPI-125) Enantiomer of the present invention (−)3-((S)-((2S,5R)-4-allyl-2,5-dimethyl-1-piperazinyl)(3-thienyl) methyl)phenol (SSR).

Compound 3
(DPI-165) Enantiomer included in Compound 1; (+)3-((R)-((2R,5S)-4-allyl-2,5-dimethyl-1-piperazinyl)(3-thienyl)methyl)phenol (RRS).

Compound 4
(DPI-1198W92) A racemic mixture (±)3-((R*)-((2S*, 5R*)-4-allyl-2,5-dimethyl-1-piperazinyl)(3-thienyl)methyl) phenol which includes enantiomers (+)-3-((R)-((2S,5R)-4-allyl-2,5-dimethyl-1-piperazinyl)(3-thienyl)methyl)phenol and (−)3-((S)-((2R,5S)-4-allyl-2,5-dimethyl-1-piperazinyl) (3-thienyl)methyl)phenol (RSR and SRS).

Compound 5
(ARD-444) Enantiomer included in Compound 4: (+)-3-((R)-((2S,5R)-4-allyl-2,5-dimethyl-1-piperazinyl)(3-thienyl)methyl)phenol (RSR).

Compound 6
(DPI-3553W92) Enantiomer included in Compound 4: (−)3-((S)-((2R,5S)-4-allyl-2,5-dimethyl-1-piperazinyl)(3-thienyl)methyl)phenol (SRS).

The results of the radioligand binding assays are set forth below in Table I:

TABLE I

| Compound | | Rat Brain Membrane $K_1$ (nM) | | | Guinea Pig Brain Membrane $K_1$ (nM) |
|---|---|---|---|---|---|
| # | Type | $\mu$ | $\delta$ | | $\kappa$ |
| 1 | Racemic Mixture DPI-1197W92 (RRS and SSR) | 0.36 | 1.29 | | 1.67 |
| 2 | Enantiomer DPI-125 (SSR) | 0.40 | 0.88 | | 1.77 |
| 3 | Enantiomer DPI-165 (RRS) | 658 | 744 | | 100 |
| 4 | Racemic Mixture DPI-1198W92 (RSR and SRS) | 0.18 | 14.9 | | 2.34 |
| 5 | Enantiomer ARD-444 (RSR) | 0.75 | 113 | | 1.73 |
| 6 | Enantiomer DPI-3553W92 (SRS) | 60 | 13 | | 16 |

Results: It is evident that each compound exhibits distinct and different binding affinity for the different types of receptors tested. The strong and increased affinity of the compound DPI-125 for both mu and delta receptors is shown by the very low concentration required to inhibit the approximately 1/1000 of the $K_1$ of its enantiomer DPI-165.

EXAMPLE 3

The compound of formula (I) and compounds 1, 3, 4, 5 and 6 as identified above, were evaluated for in vitro opioid receptor activity in various receptor systems, including mouse vas deferens (Mouse Vas Deferens $ED_{50}$), and guinea pig ileum (Guinea Pig Ileum $ED_{50}$). The assay procedures used for such determinations of receptor activity are set out below.

In vitro bioassays: Mouse vasa deferentia (MVD), CD-1 binding of the labeled compounds. The $K_1$ of DPI-125 is strain, Harlan, Raleigh, N.C.) were removed from mice and suspended between platinum electrodes with 0.5 g of tension in organ bath chambers containing a modified $Mg^{++}$ free Krebs buffer of the following composition (millimolar): NaCl, 117.5; KCl, 4.75; $CaCl_2$, 2.6; $KH_2PO_4$, 1.20; $NaHCO_3$, 24.5; and glucose, 11. The buffer was saturated with 95% $O_2$/5% $CO_2$ and kept at 37° C. Tissues were stimulated at supramaximal voltage with 10-Hz pulse trains for 400-msec.; train interval 10 seconds; and 1.0 msec pulse duration at maximal voltage. Delta receptor activity was determined by adding appropriate concentrations of test compound to organ baths and allowing a maximal response before addition of the next higher concentration. Mu receptor activity was determined in similar fashion, but in the presence of 3 $\mu$M TIPP (a highly selective delta antagonist; P. W. Schiller, T. M.-D. Nguyen, G. Weltrowska, B. C. Wilkes, B. J. Marsden, C. Lemieux, and N. N. Chung, *Proc. Natl. Acad. Sci.* 89, 11871 (1992)) and 15 nM nor-BNI (a selective kappa antagonist; P. S. Portoghese, A. W. Lipkowski, and A. E. Takemori, *Life Sci.* 40, 1287 (1987)).

Intact ileums (about 3 cm length) were removed from guinea pig and suspended with 1 g of tension in a bath chamber as described for the vasa deferentia. The ileums were stimulated with electrical square-wave pulses of 0.1-Hz, 1 msec pulse duration at supramaximal voltage.

The percentage inhibition of the electrically induced muscle contractions was determined for the compounds at varying cumulative concentrations. The $ED_{50}$ values were extrapolated from curves showing the dose concentration plotted against the response (J. A. H. Lord, A. A. Waterfield, J. Hughes, H. W. Kosterlitz, *Nature* 267, 495, (1977)). The results are set forth in Table II as shown below:

TABLE II

| Compound | Type | Mouse Vas Deferens $ED_{50}$ (nM) | | Guinea Pig Ileum $ED_{50}$ (nM) |
|---|---|---|---|---|
| | | $\mu$ | $\delta$ | $\mu$ |
| 1 | DPI-1197W92 Racemic Mixture (RRS and SSR) | 881 | 30 | 5.5 |
| 2 | DPI-125 Enantiomer (SSR) | 38.8 | 14.2 | |
| 3 | DPI-165 Enantiomer (RRS) | >1000 | >1000 | |
| 4 | DPI-1198W92 Racemic Mixture (RSR and SRS) | 170 | 58 | 2.3 |
| 5 | ARD-444 Enantiomer (RSR) | 79.3 | 1.3 | |
| 6 | DPI-3553W92 Enantiomer (SRS) | >1000 | 282 | 365 |

EXAMPLE 4

Analgesia was assayed in rats using the tail pinch test with simultaneous monitoring of capillary blood gases ($pCO_2$). During this testing period respiratory depression values were also obtained. Male rats (Wistar Hannover 200–300 g) were anesthetized with 2% isoflurane (J. A. Webster, Inc., Sterling, Mass. The femoral artery was cannulated with PE50 tubing for blood sampling. The external jugular vein was also cannulated with Silastic tubing for drug injection. After surgery, anesthetic gases were removed and the rat was allowed to rest in a plastic restrainer for 60 minutes to establish baseline values of blood gases.

The compounds 1–6 were administered intravenous. Nociceptive response and respiratory values were obtained for a 1–2 hour period. The femoral artery cannulation was used to draw arterial blood into a syringe pre-wetted with heparin. Samples were then analyzed with a blood gas analyzer (Ph/Gas Analyzer Synthesis 25 Model, Instrumentation Laboratory) to assess respiratory depression effects. The volume of blood taken each time was 0.15 cc. The syringes were capped immediately and the blood gases analyzed within 5 minutes. The blood exposed to air at the tip of the syringe was expelled. The blood was mixed by gentle inversion and an aliquots of 0.10 cc was injected into the blood gas analyzer.

The gas analyzer was well maintained and operated. Calibrations (low, normal and high) were done at the beginning of every day of testing. The sample lines, co-oximeter and the blood gas electrode were cleaned regularly at the end of every day of testing. Hematocrit calibration (high and low) was scheduled on a weekly basis and tubing, sample and pinch valve were replaced on a monthly basis.

An artery clamp was placed on the tail (one inch from the tip of the tail) for a short duration until an escape response occurred (i.e. tail-flick or vocalization). The escape response latency was recorded by means of a stopwatch. A cutoff time of 20 sec. was used to prevent unnecessary tissue damage. Rats were observed for nociceptive responses of vocalization or painful body movements. The elapsed time to elicit a pain response was recorded as the tail pinch latency in seconds. Blood gases were monitored at approximately the same time points as the tail pinch test.

The ED50 values for analgesia potency and respiratory depression were determined to calculate the safety or therapeutic ratio, which is defined as the respiratory depression ED50 divided by analgesia ED50. The analgesic potency (half maximum effective dose, ED50) was determined by the dose at which half of the animals did not show any nociceptive response to the artery clamp pressure within 20 seconds. As shown in Table III, the safety ratio of (−)3-((S)-((2S,5R)-4-allyl-2,5-dimethyl-1-piperazinyl)(3-thienyl) methyl)phenol is unexpectedly much greater than either of the racemic mixtures and any of the other enantiomers tested.

TABLE III

| Compound | Type | Respiratory Depression $ED_{50}$ mg/kg | Analgesia $ED_{50}$ mg/kg | Safety Ratio |
|---|---|---|---|---|
| 1 | DPI-1197W92 Racemic Mixture (SSR and RRS) | 0.98 | 0.21 | 4.7 |
| 2 | DPI-125 Enantiomer (SSR) | 0.72 | 0.046 | 15.7 |
| 3 | DPI-165 Enantiomer (RRS) | >6.0 | >6.0 | Indeterminate |
| 4 | DPI-1198W92 Racemic Mixture (RSR and SRS) | 0.12 | 0.05 | 2.4 |
| 5 | ARD-444 Enantiomer (RSR) | 0.067 | 0.03 | 2.2 |
| 6 | DPI-3553W92 Enantiomer (SRS) | >6.0 | >6.0 | Indeterminate |

As can be seen by the above results, the safety ratio for (−)3-((S)-((2S,5R)-4-allyl-2,5-dimethyl-1-piperazinyl)(3-thienyl)methyl)phenol is at least three (3) times greater than either of the racemic mixtures and at least six times greater than any of the other enantiomeric compounds tested. Thus, the use of (−)3-((S)-((2S,5R)-4-allyl-2,5-dimethyl-1-piperazinyl)(3-thienyl)methyl)phenol provides for the beneficial effects of analgesia with a substantially reduced risk of respiratory depression.

EXAMPLE 5

The results of the tail pinch test and levels of $CO_2$ determined from the sampled blood are plotted in FIGS. 1–6. The following Table IV illustrates the results in a simple format to show the unexpected and superior effectiveness of the presently claimed enantiomeric compound (−)3-((S)-((2S,5R)-4-allyl-2,5-dimethyl-1-piperazinyl)(3-thienyl)methyl)phenol.

TABLE IV

| | | Respiratory Depression % Units Baseline $pCO_2$ at 0.30 mg/kg | | | Analgesia (delay of response to tail pinch) (sec units) at 0.30 mg/kg | | |
|---|---|---|---|---|---|---|---|
| Figure | Compound | 4 min. | 8 min. | 32 min. | 4 min. | 8 min. | 32 min. |
| FIG. 1 | Compound 1 DPI-1197W92 Racemic Mixture (RRS and SSR) | 21% | 25% | 7% | 19.5 | 10.5 | 1 |

TABLE IV-continued

Figure 2:
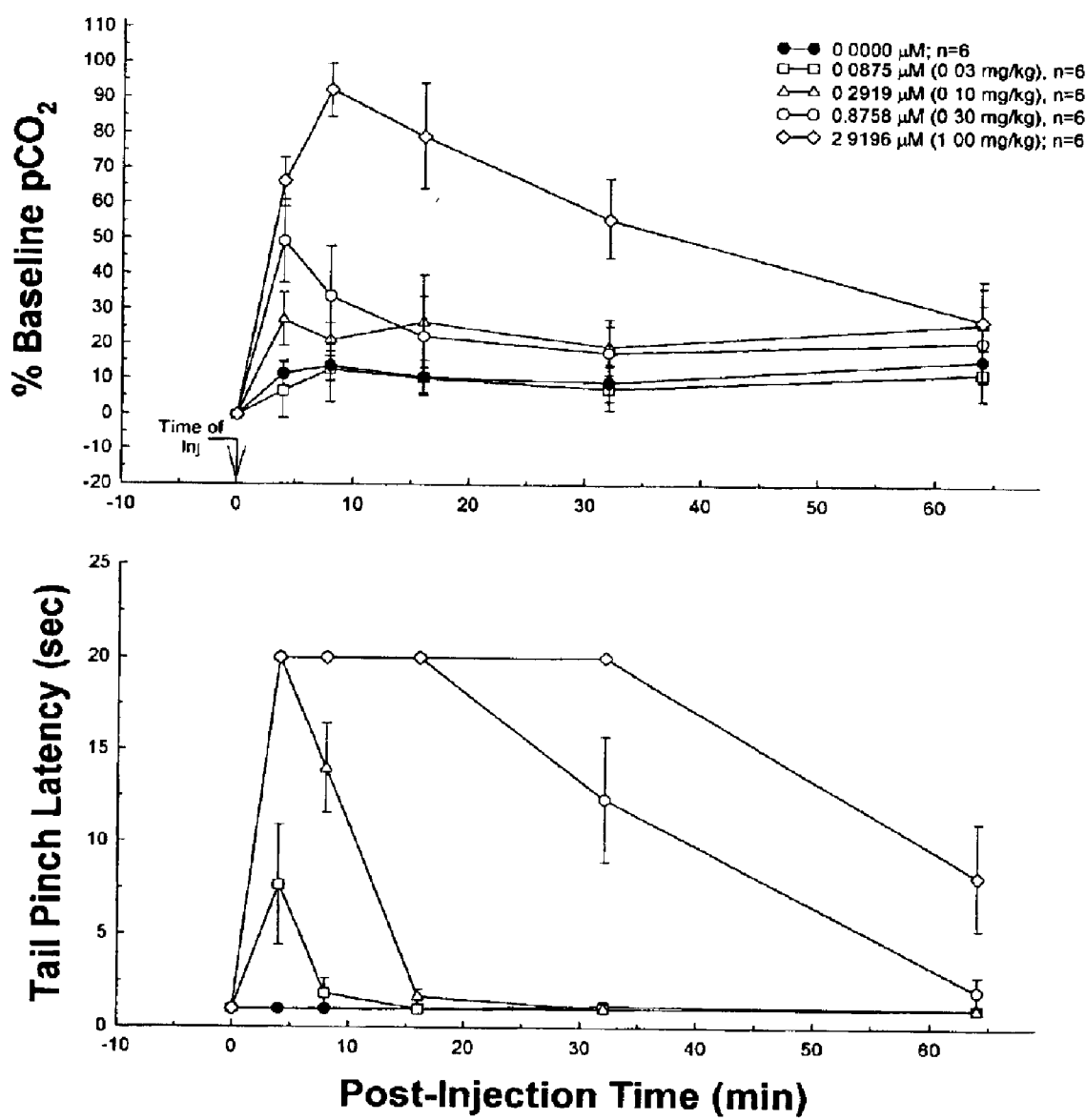
FIG. 2 shows the highly effective results of (-)3-((S)-((2S,5R)-4-allyl-2,5-dimethyl-1-piperazinyl)(3-thienyl)methyl)phenol, the compound of the present invention, on analgesia and respiratory depression in test animals.
Figure 3:
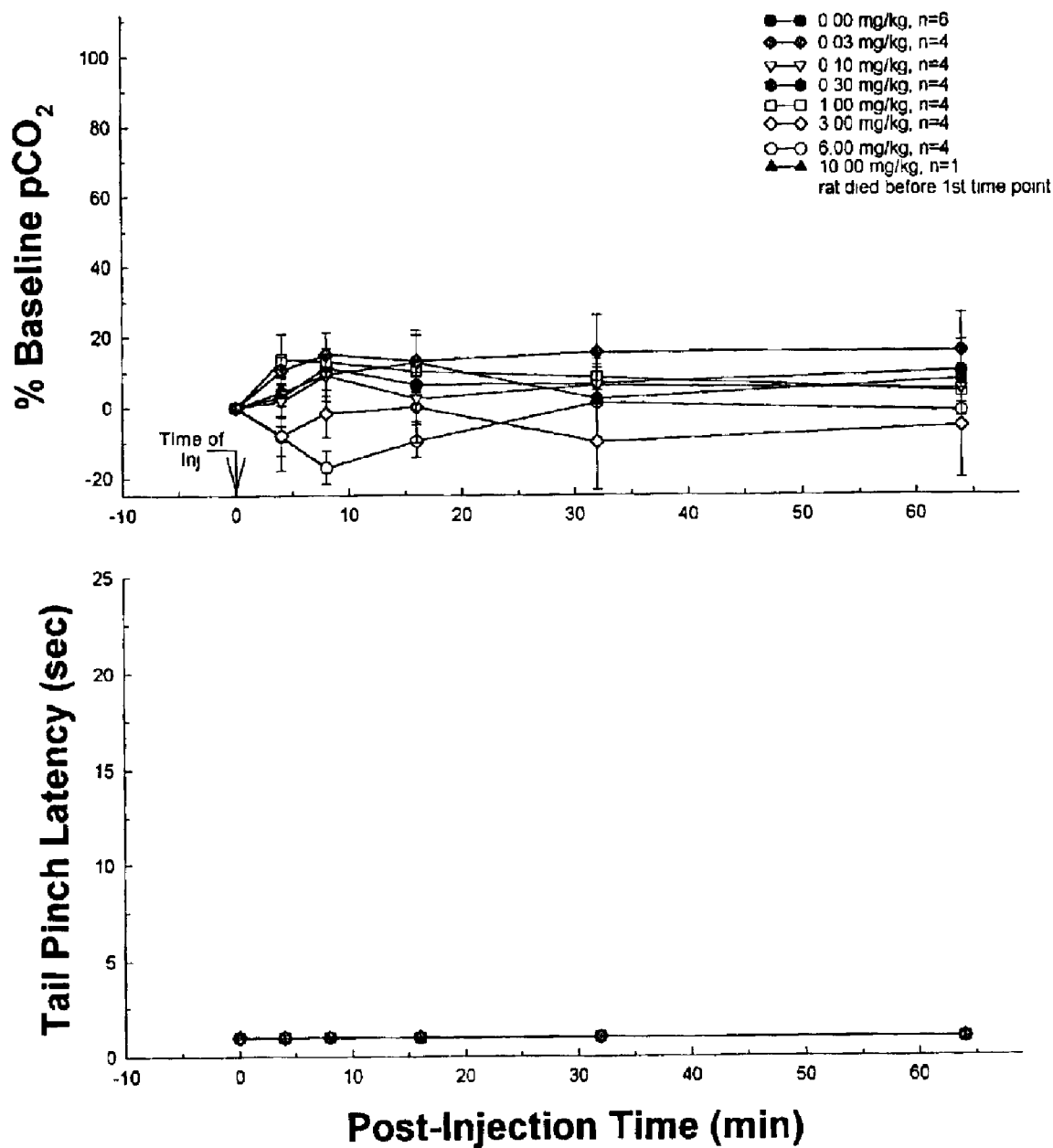
FIG. 3 shows the effects of DPI-165 on analgesia and respiratory depression in test animals.
Figure 4:
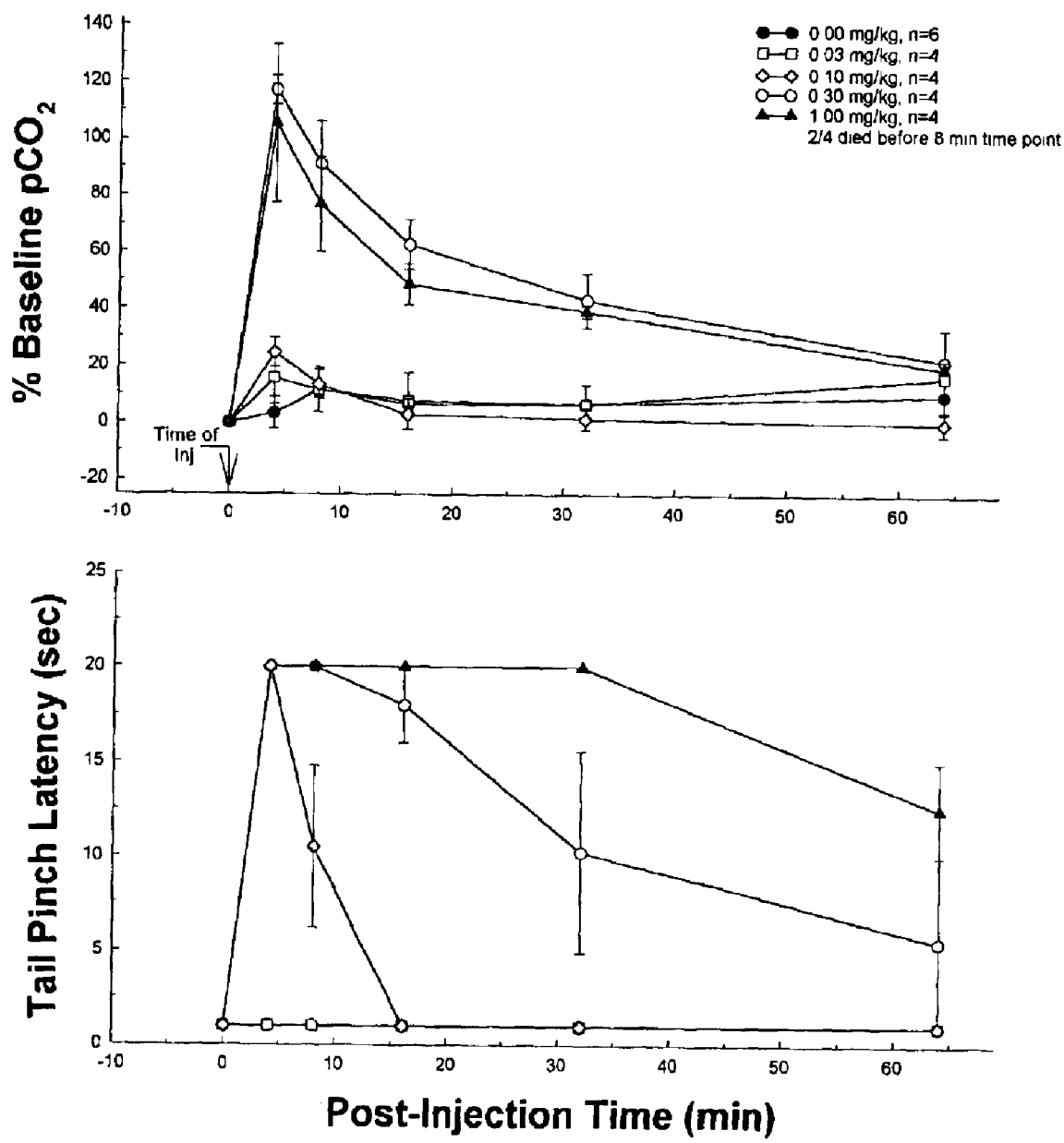
FIG. 4 shows the effects of racemic mixture DPI-1198W92 on analgesia and respiratory depression in test animals.
Figure 5:
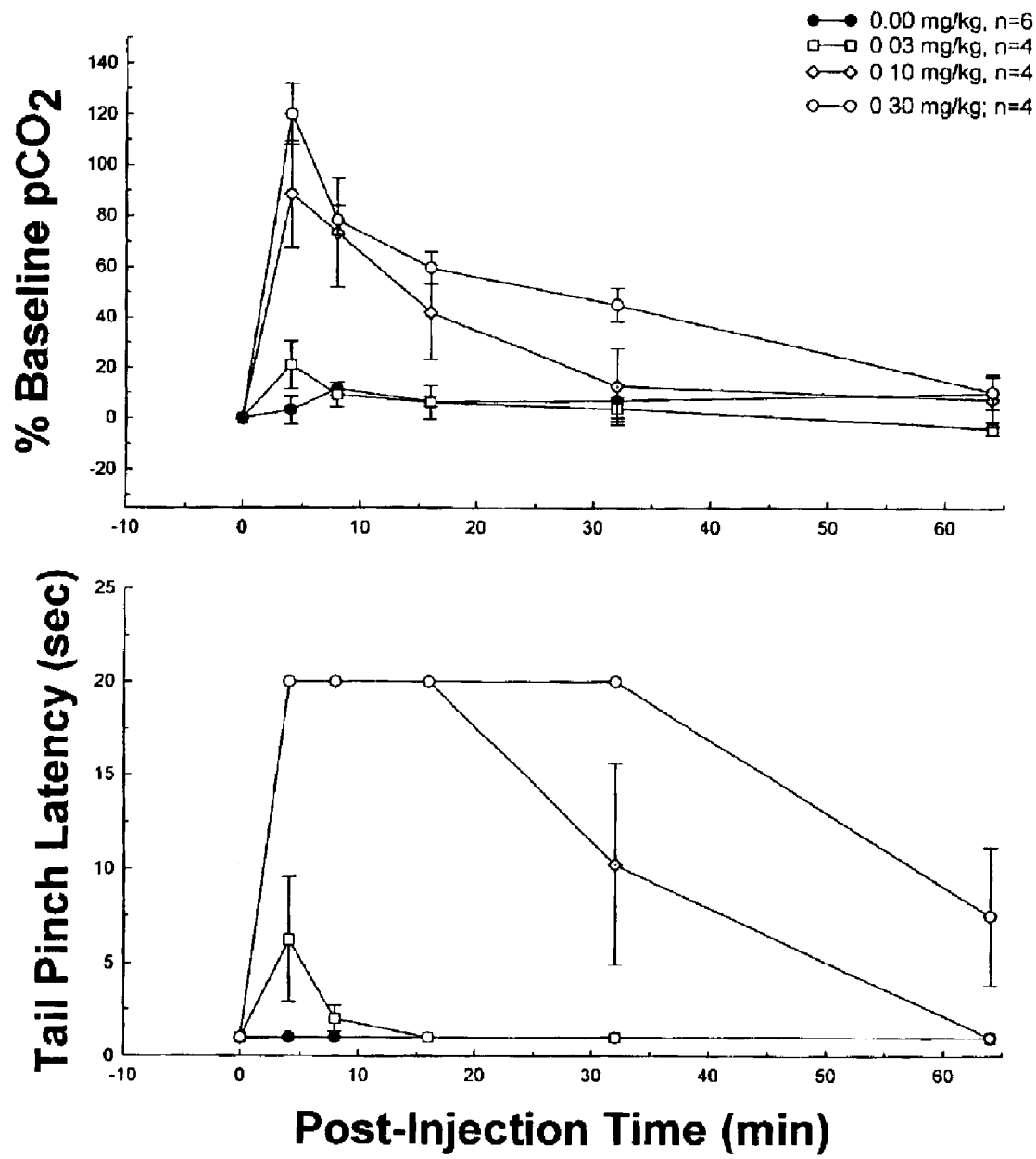
FIG. 5 shows the effect of ARD-444 on analgesia and respiratory depression in test animals.
Figure 6:
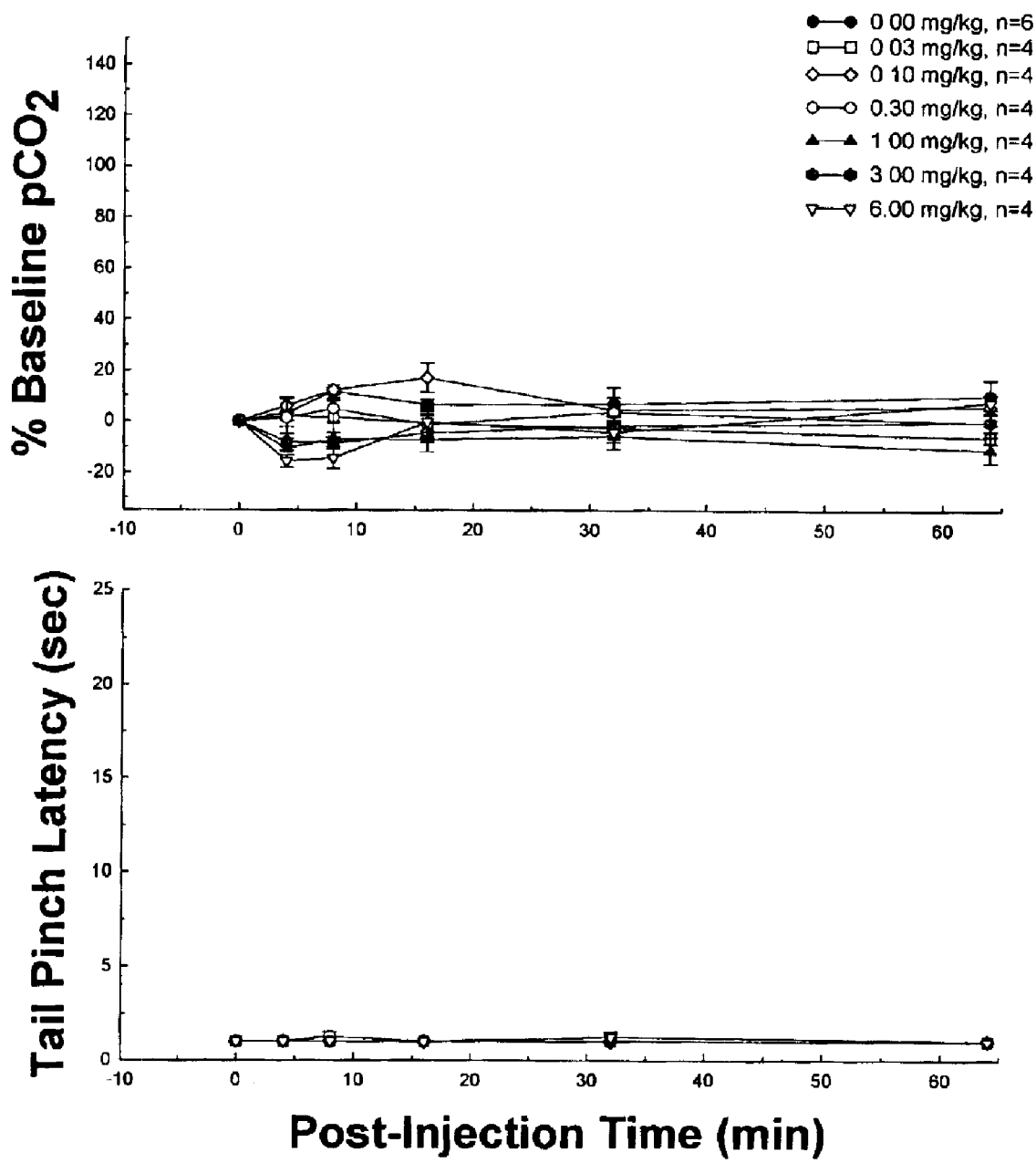
FIG. 6 shows the effect of DPI-3553W92 on analgesia and respiratory depression in test animals.

| | | Respiratory Depression % Units Baseline pCO$_2$ at 0.30 mg/kg | | | Analgesia (delay of response to tail pinch) (sec units) at 0.30 mg/kg | | |
|---|---|---|---|---|---|---|---|
| Figure | Compound | 4 min. | 8 min. | 32 min. | 4 min. | 8 min. | 32 min. |
| FIG. 2 | Compound 2 DPI-125 Claimed enantiomer (SSR) | 48% | 34% | 17% | 20 | 20 | 12.3 |
| FIG. 3 | Compound 3 DPI-165 Enantiomer (RRS) | 0 | 0 | 0 | 0 | 0 | 0 |
| FIG. 4 | Compound 4 DPI-1198W92 Racemic Mixture (RSR and SRS) | 117% | 91% | 43% | 20 | 20 | 10 |
| FIG. 5 | Compound 5 ARD-444 Enantiomer (RSR) | 120% | 78% | 45% | 20 | 20 | 20 |
| FIG. 6 | Compound 6 DPI-3553W92 Enantiomer (SRS) | 0 | 0 | 0 | 0 | 0 | 0 |

As shown above and in FIGS. 1–6, the enantiomerically pure claimed compound (−)3-((S)-((2S,5R)-4-allyl-2,5-dimethyl-1-piperazinyl)(3-thienyl)methyl)phenol (DPI-125) safely maintains analgesia for an extended time without lethal respiratory depression. The two other compounds that maintained the analgesia for greater than 32 minutes were the racemic mixture DPI-1198W92 (Compound 4, (RSR and SRS)) and one of its components ARD-444 (Compound 5, RSR), but several of the test subjects died during the testing regime due to complete respiratory depression (respiratory failure). DPI-165 (Compound 3, (RRS)) and DPI-3553W92 (Compound 6, (SRS)) produced no measurable analgesic effect and no effect on blood pCO$_2$ levels and thus no respiratory depression. DPI-1197W92 (Compound 1, (RRS and SSR)) provided only limited analgesia for a short time and by 32 minutes into the testing period no analgesia effect remained. The results clearly show the unexpected effectiveness of the claimed compound relative to the other tested compounds. (−)3-((S)-((2S,5R)-4-Allyl-2,5-dimethyl-1-piperazinyl)(3-thienyl)methyl)phenol provides extended analgesia beyond any other tested compound with substantially lower respiratory depression and mortality for the same effective analgesic effect.

EXAMPLE 6

Experiments are carried out to determine the effects of the claimed compound (−)3((S)-((2S,5R)-4-Allyl-2,5-dimethyl-1-piperazinyl)(3-thienyl)methyl)phenol on respiratory depression and analgesia induced by i.v. infusion of alfentanil or fentanyl, both of which are potent mu agonists. Respiratory depression effects are measured by analyzing rat blood gases for pCO$_2$ levels. Rat blood samples are drawn and analyzed for CO$_2$ content following a continuous i.v. infusion of alfentanil (6 mg/min) and an i.v. bolus injection of various doses of the claimed compound (−)3-((S)-((2S,5R)-4-Allyl-2,5-dimethyl-1-piperazinyl)(3-thienyl)methyl)phenol.

Blood CO$_2$ levels are observed as an indication of respiratory depression as a result of alfentanil administration and (−)3-((S)-((2S,5R)-4-Allyl-2,5-dimethyl-1-piperazinyl)(3-thienyl)methyl)phenol (DPI-125). Analgesia is also assessed with a tail-pinch method at the same time points that blood is drawn to determine blockage of respiratory depression by (−)3-((S)-((2S,5R)-4-Allyl-2,5-dimethyl-1-piperazinyl)(3-thienyl)methyl)phenol (DPI-125) but not the analgesia induced by alfentanil.

Overall, the claimed compound (−)3-((S)-((2S,5R)-4-Allyl-2,5-dimethyl-1-piperazinyl)(3-thienyl)methyl)phenol is useful clinically in intraoperative, postoperative and chronic pain applications to attenuate the respiratory depression and maintain the analgesic effects of mu opioid receptor analgesics.

EXAMPLE 7

The following describes a procedure that provided observations on the emesis effects of (−)-3-((S)-((2S,5R)-4-allyl-2,5-dimethyl-1-piperazinyl)(3-thienyl)methyl)phenol (DPI-125). Three adult male beagle dogs were separately administered (−)-3-((S)-((2S,5R)-4-allyl-2,5-dimethyl-1-piperazinyl)(3-thienyl)methyl)phenol (DPI-125) in escalating dosages. Doses were chosen to produce blood levels consistent with strong to extreme analgesia and that would produce obvious pharmacological effects including lethargy and sedation. The compound was dissolved in sterile 5% dextrose solution that was buffered with acetic acid/sodium acetate buffer and administered intravenously in a slow bolus injection over 1–2 minutes. Firstly, the three dogs were administered test volume dosages of buffered 5% dextrose to ensure there was no reaction to the vehicle. Secondly, (−)3-((S)-((2S,5R)-4-allyl-2,5-dimethyl-1-piperazinyl)(3-thienyl)methyl)phenol (DPI-125) was administered in single injections at escalating dosages of 0.1, 0.3 and 0.5 mg/kg, with an intervening seven-day period before giving the next highest dose. No retching or vomiting was observed with any of the dogs at any of the doses.

Nausea and vomiting are common and expected adverse consequences of conventional mu opiates such as morphine and fentanyl, as well as for mixed delta/mu opioid analgesics, in both dogs and humans. Dogs are regarded as being a species particularly sensitive to the pro-emetic effects of opiates. From the above test results, it is apparent that the pharmaceutical composition according to the present invention comprising (−)-3-((S)-((2S,5R)-4-allyl-2,5-dimethyl-1-piperazinyl)(3-thienyl)methyl)phenol (DPI-125)

is excellent in safety and unexpectedly eliminated the negative side effects of nausea and vomiting that typically occurs with the administration of an opioid analgesic.

Typically, mu agonists produce a substantial beneficial effect of analgesia and many adverse side effects, such as respiratory depression, nausea, addiction and dependence. The ability to use the compound (−)3-((S)-((2S,5R)-4-Allyl-2,5-dimethyl-1-piperazinyl)(3-thienyl)methyl)phenol to block the unwanted side effects of mu agonists permits physicians to increase the administration of analgesics because of reduced concerns about respiratory depression. Patients experience less pain after an operation and require less postoperative care by hospital staff. The overall lifestyle of patients taking mu opioids may be significantly improved with the concurrent use of the compound (−)3-((S)-((2S,5R)-4-Allyl-2,5-dimethyl-1-piperazinyl)(3-thienyl)methyl)phenol.

That which is claimed is:

1. An essentially pure compound of the formula:

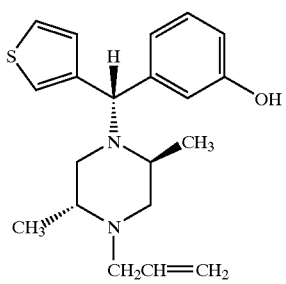

(I)

(−)3-((S)-((2S,5R)-4-allyl-2,5-dimethyl-1-piperazinyl)(3-thienyl)methyl)phenol or a pharmaceutically acceptable salt thereof.

2. (−)3-((S)-((2S,5R)-4-allyl-2,5-dimethyl-1-piperazinyl)(3-thienyl)methyl)phenol or a pharmaceutically acceptable salt thereof having an enantiopurity of at least 98%.

3. (−)3-((S)-((2S,5R)-4-allyl-2,5-dimethyl-1-piperazinyl)(3-thienyl)methyl)phenol or a pharmaceutically acceptable salt thereof having an enantiopurity of at least 99%.

4. A pharmaceutical composition comprising a compound of claim 1 and a pharmaceutically acceptable carrier therefor.

5. A pharmaceutical composition comprising:

(a) an effective amount of a bioactive agent for treatment of a condition selected from the group consisting of drug addiction, alcohol addiction, drug overdose, mental illness, cough, lung edema, gastro-intestinal disorders, arthritis, psoriasis, asthma, inflammatory bowel disease, disorders of respiratory function, functional bowel disease, irritable bowel syndrome, diarrhea, functional distension, functional pain, non-ulcerogenic dyspepsia, organ transplant rejection, skin graft rejection, cardiac disorders, mental disorders, emotional disorders, cognitive disorders; emesis; respiratory depression; acne and skin lesions; and (b) an effective amount of a compound comprising the formula:

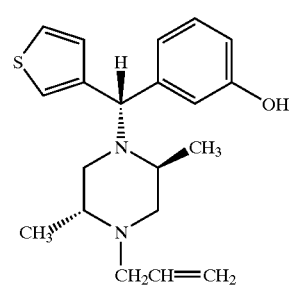

(I)

(−)3-((S)-((2S,5R)-4-allyl-2,5-dimethyl-1-piperazinyl)(3-thienyl)methyl)phenol or a pharmaceutically acceptable salt thereof.

6. A method of treating pain in an animal which comprises administering to an animal an effective amount of a compound of claim 1.

7. The method of claim 6, wherein the animal is a human.

8. The method of claim 6, wherein the compound is administered by a mode of administration selected from the group consisting of parenteral, non-parenteral, oral, rectal, topical, nasal, ophthalmic, subcutaneous, intramuscular, intravenous, transdermal, spinal, intrathecal, intra-articular, intra-arterial, sub-arachnoid, sublingual, oral mucosal, bronchial, lymphatic, and intra-uterine administration.

9. A method of effecting a receptor-mediated analgesia of an animal in need of same comprising administering to the animal an effective amount of the compound of claim 1.

10. A method for treatment of one or more conditions selected from the group consisting of cough, functional diarrhea, and functional pain, comprising administration to a subject in need of such treatment an effective amount of a compound of claim 1.

11. A method of reducing, treating or preventing drug-mediated respiratory depression in an animal caused by a mu opioid receptor binding agent, comprising:
administering to the animal a pharmaceutical composition comprising:
(1) an effective amount of a mu opioid receptor binding agent that acts on mu opioid receptors and has a respiratory depression side effect, and
(2) an effective amount of a compound of the formula:

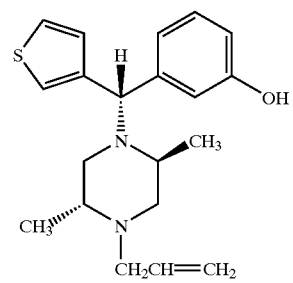

(I)

(−)3-((S)-((2S,5R)-4-allyl-2,5-dimethyl-1-piperazinyl)(3-thienyl)methyl)phenol or a pharmaceutically acceptable salt thereof, wherein the compound acts to attenuate the respiratory depression side effect of the mu opioid receptor binding agent without precluding the therapeutic efficacy of the mu opioid receptor binding agent.

12. The method according to claim 11, wherein the mu opioid receptor binding agent is selected from the group consisting of anesthetics and analgesics.

13. The method according to claim 11, wherein the mu opioid receptor binding agent comprises an analgesic agent selected from the group consisting of morphine, alfentanil, morphine-6-glucoronide, oxymorphone, hydromorphone, oxycodone, hydrocodone, fentanyl, meperidine, sufentanyl and codeine.

14. A method for screening opioid respiratory depression-suppressing compounds, comprising conducting activity reversal assays of a candidate respiratory depression-suppressing compound in receptor tissue to determine if the candidate respiratory depression-suppressing compound transductionally mediates a respiratory depression suppressing effect in the receptor tissue, in response to a respiration-depressing composition, wherein said activity reversal assays are conducted comparatively, in the absence and in the presence of an anti-suppression compound of the formula:

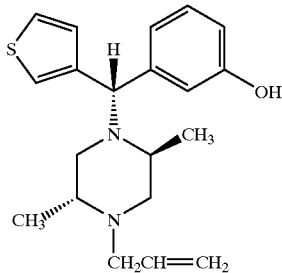

(I)

(−)3-((S)-((2S,5R)-4-allyl-2,5-dimethyl-1-piperazinyl)(3-thienyl)methyl)phenol or a pharmaceutically acceptable salt thereof, to determine if the activity of the candidate compound is substantially reversed at the tissue site by the presence of the anti-suppression compound of formula (I), thereby indicating the candidate respiratory depression-suppressing compound as possessing potential bioefficacy for suppressing respiratory depression effects incident to the use of other therapeutic agents.

15. A method of effecting a receptor-mediated analgesia of an animal in need of same without inducing nausea or vomiting comprising administering to the animal an effective amount of the compound of claim 1 to effect receptor-mediated analgesia without inducing nausea or vomiting.

16. The method according to claim 15, wherein the animal is a human.

17. A method of effecting a receptor-mediated response of an animal in need of same comprising administering to the animal an effective amount of the compound of claim 1 to effect receptor-mediated response without inducing nausea or vomiting, wherein the opioid receptor-mediated response is selected from the group consisting of analgesia, reduced coughing, reduced functional pain and reduced functional diarrhea.

18. The compound according to claim 1, further comprising a pharmaceutically acceptable ester of formula I wherein the ester is selected from the group consisting of:

a) carboxylic acid esters of the hydroxyl group of the compound of formula (I) wherein a non-carbonyl moiety of the carboxylic acid portion of the ester grouping is selected from straight or branched chain alkyl, alkoxyalkyl, arylalkyl, aryloxyalky, aryl;

b) amino acid esters;

c) dicarboxylic acid esters; and d) carbonate esters; carbamate esters; and inorganic esters.

* * * * *